US009474474B2

(12) United States Patent
Lamego et al.

(10) Patent No.: US 9,474,474 B2
(45) Date of Patent: Oct. 25, 2016

(54) PATIENT MONITOR AS A MINIMALLY INVASIVE GLUCOMETER

(71) Applicant: Cercacor Laboratories, Inc., Irvine, CA (US)

(72) Inventors: Marcelo M. Lamego, Cupertino, CA (US); Jeroen Poeze, Rancho Santa Margarita, CA (US); Cristiano Dalvi, Lake Forest, CA (US); Hung Vo, Fountain Valley, CA (US); Ferdyan Lesmana, Irvine, CA (US); Gregory A. Olsen, Trabuco Canyon, CA (US); Sean Merritt, Lake Forest, CA (US); Ashish Patel, La Habra, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

(21) Appl. No.: 14/196,300

(22) Filed: Mar. 4, 2014

(65) Prior Publication Data

US 2014/0275881 A1    Sep. 18, 2014

Related U.S. Application Data

(60) Provisional application No. 61/782,923, filed on Mar. 14, 2013.

(51) Int. Cl.
*A61B 5/145* (2006.01)
*A61B 5/1455* (2006.01)

(52) U.S. Cl.
CPC ......... *A61B 5/14532* (2013.01); *A61B 5/1455* (2013.01); *A61B 5/14542* (2013.01); *A61B 2560/045* (2013.01)

(58) Field of Classification Search
CPC .................. A61B 5/14532; A61B 5/1455
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |

(Continued)

FOREIGN PATENT DOCUMENTS

| | | |
|---|---|---|
| WO | WO 01/28416 A1 | 4/2001 |
| WO | WO 2012/075322 A2 | 6/2012 |
| WO | WO 2014/158820 A1 | 10/2014 |

OTHER PUBLICATIONS

International Seach Report and Written Opinion for International Application No. PCT/US2014/020359, dated Jul. 4, 2014.

(Continued)

*Primary Examiner* — Sam P Siefke
(74) *Attorney, Agent, or Firm* — Knobbe, Martens, Olson & Bear LLP

(57) ABSTRACT

In an embodiment, a patient monitor, such as a pulse oximeter, functions as a spot check glucometer when in communication with a blood glucose strip reader. In an embodiment, communications between the patient monitor and the strip reader may optionally be encrypted. Embodiments also include the strip reader housed in a dongle configured to mate with a sensor port of the pulse oximeter.

17 Claims, 15 Drawing Sheets

(56) References Cited

U.S. PATENT DOCUMENTS

| | | |
|---|---|---|
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,790,178 B1 * | 9/2004 | Mault et al. ................ 600/300 |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B2 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |

(56) References Cited

U.S. PATENT DOCUMENTS

| | | |
|---|---|---|
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | AlAli et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |

(56) References Cited

U.S. PATENT DOCUMENTS

| | | |
|---|---|---|
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 2008/0097909 A1* | 4/2008 | Dicks .................. G06Q 50/24 705/50 |
| 2008/0221404 A1 | 9/2008 | Tso |
| 2011/0213218 A1 | 9/2011 | Weiner et al. |

OTHER PUBLICATIONS

International Preliminary Report on Patentability mailed Sep. 24, 2015 for PCT Application No. PCT/US2014/020359.

* cited by examiner

PATIENT MONITOR AS A MINIMALLY INVASIVE GLUCOMETER

CROSS REFERENCE TO RELATED APPLICATION

This application claims the benefit of priority under 35 U.S.C. §119(e) of U.S. Provisional Application No. 61/782,923, filed Mar. 14, 2013, the disclosure of which is hereby incorporated by reference herein in its entirety for all purposes.

BACKGROUND

The present application relates to the field of physiological monitoring devices. Specifically, the present application relates to the field of glucometers.

Health care providers have long recognized the need to monitor patients' analyte levels, including for example, oxygen saturation, carboxy hemoglobin, methemoglobin, total hemoglobin and glucose levels, as well as other physiological parameters, including for example, pulse rate, perfusion, hydration, overall wellness, pH, bilirubin, sepsis and others. Specifically, low blood glucose may lead to anxiety, weakness, and in extreme cases coma and death. Likewise, high blood glucose is associated with acidosis, diabetes, glucose spilling into the urine, polyurea, hemoconcentration and related stresses on organ systems, including the renal and cardiovascular systems. Glycemic control may be particularly important in the critical care setting, where high or low blood glucose has been related to increased morbidity and mortality, although many other uses are advantageous, including self blood sugar monitoring, fitness applications, and the like.

The standard of care in caregiver environments also includes patient monitoring through spectroscopic analysis using, for example, a pulse oximeter. Medical device manufacturers are continually increasing the processing capabilities of patient monitors, such as pulse oximeters, which process signals based on attenuation of light by patient tissue. In general, such patient monitoring systems include one or more optical sensors that irradiate tissue of a patient and one or more photodetectors that detect the radiation after attenuation thereof by the tissue. The sensor communicates the detected signal to a patient monitor, where the monitor often removes noise and preprocesses the signal. Advanced signal processors then perform time domain and/or frequency domain processing to determine measurements of blood constituents and other physiological parameters of the patient.

Manufacturers have advanced basic pulse oximeters that determine measurements for blood oxygen saturation ("SpO2"), pulse rate ("PR") and pethysmographic information, to read-through-motion oximeters, to co-oximeters that determine measurements of many constituents of circulating blood. For example, Masimo Corporation of Irvine Calif. ("Masimo") manufactures pulse oximetry systems including Masimo SET® low noise optical sensors and read through motion pulse oximetry monitors for measuring Sp02, PR, perfusion index ("PI") and others. Masimo sensors include any of LNOP®, LNCS®, SofTouch™ and Blue™ adhesive or reusable sensors. Masimo oximetry monitors include any of Rad-8®, Rad-5®, Rad®-5v or SatShare® monitors.

Many innovations improving the measurement of blood constituents are described in at least U.S. Pat. Nos. 6,770,028; 6,658,276; 6,157,850; 6,002,952; 5,769,785 and 5,758,644, which are each incorporated by reference in their entirety herein for all purposes. Corresponding low noise optical sensors are disclosed in at least U.S. Pat. Nos. 6,985,764; 6,088,607; 5,782,757 and 5,638,818, which are each incorporated by reference in their entirety herein for all purposes.

Masimo also manufactures advanced co-oximeters including Masimo Rainbow® SET, which provides measurements in addition to Sp02, such as total hemoglobin (SpHb™), oxygen content (SpCO™), methemoglobin (SpMet®), carboxyhemoglobin (SpCO®) and PVI®. Advanced blood parameter sensors include Masimo Rainbow® adhesive, ReSposable™ and reusable sensors. Masimo's advanced blood parameter monitors include Masimo Radical-7™, Rad-87™, and Rad-57™ monitors as well as Pronto and Pronto-7 spot check monitors.

Many innovations relating to the foregoing technologies are described in at least U.S. Pat. Nos. 7,647,083; 7,729,733; U.S. Pat. Pub. Nos. 2006/0211925; and 2006/0238358, which are each incorporated by reference in their entirety herein for all purposes.

These and other instruments have gained rapid acceptance in a wide variety of medical applications, including surgical wards, intensive care and neonatal units, general wards, home care, physical training, and virtually all types of monitoring scenarios.

SUMMARY

In an embodiment, a patient monitor, such as a pulse oximeter, co-oximeter, or other patient monitor ("patient monitor"), functions as a glucometer when in communication with a blood glucose strip reader. In various embodiments, communications between the patient monitor and the strip reader may optionally be encrypted, may implement authorization and/or authentication protocols or the like, or may implement quality control by providing authorized strip readers to communicate with the monitor.

In an embodiment, a spot check monitoring system using a monitor configured to accept signals responsive to light attenuated by body tissue is disclosed which comprises: a minimally invasive glucose reader; and a patient monitor in communication with said minimally invasive glucose reader, wherein, when a glucose level is read by said minimally invasive glucose reader, said glucose level is transmitted to said patient monitor, wherein said patient monitor is configurable as an oximeter and is configurable to display said glucose level when said glucose level is transmitted to said patient monitor.

According to an aspect, the spot check monitoring system may further comprise a dongle, wherein said dongle houses said minimally invasive glucose reader.

According to another aspect, the spot check monitoring system may further comprise a reader board, wherein said minimally invasive glucose reader is mounted on said reader board.

According to yet another aspect, the spot check monitoring system may further comprise an encryption controller configured to encrypt information from said minimally invasive glucose reader.

According to another aspect, the spot check monitoring system may further comprise an encryption board, wherein said encryption controller is mounted on said encryption board.

According to yet another aspect, said encryption board and said reader board may be different boards.

According to another aspect, the spot check monitoring system may further comprise strips configured to be read by said minimally invasive glucose reader, wherein said strips comprise source identifying strips.

According to yet another aspect, when said patient monitor is configured as said oximeter, said patient monitor communicates with an optical sensor that outputs signals responsive to light attenuated by patient tissue carrying pulsing blood, said patient monitor receiving said signals and configured to process said signals to determine physiological parameters including at least an indication of oxygen saturation of the patient tissue.

In another embodiment, a method of converting a patient monitor to a spot check glucometer is disclosed which comprises providing a minimally invasive glucose reader configured to accept strips carrying samples to be analyzed; providing a patient monitor configured to communicate with an optical sensor to receive signals responsive to light attenuated by tissue of a patient carrying pulsing blood, to process said signals, to determine one or more measurements of physiological parameters of said patient including at least oxygen saturation; associating said reader with said patient monitor causing said patient monitor to change to a spot check glucometer; inserting one of said strips into said reader; and displaying on a display of said patient monitor measurement data responsive to said sample on said inserted strip.

According to an aspect, said associating comprises establishing electrical communication between said reader and said patient monitor.

According to another aspect, said establishing electrical communication comprises attaching a dongle housing said reader.

According to yet another aspect, said establishing electrical communication comprises establishing encrypted communication with said monitor.

According to another aspect, establishing electrical communication comprises establishing communication through an encryption board.

In yet another embodiment, an encrypted source-identifying glucose strip reader configured to change an oximeter into a glucometer is disclosed which comprises a strip reader configured to accept samples on a strip and output a signal responsive to characteristics of said sample, said characteristics including a measure of glucose in said sample; a controller communicating with said strip reader to determine said measure of glucose from said sample and output data indicative of at least said measure; and an encryption controller configured to receive said data from said controller and output encrypted data to an oximeter configured to modify its operation to present display indicia to a user of the oximeter, the display indicia responsive to said measure of said glucose in said sample, the encrypted data identifying by its encryption the source of the reader.

According to an aspect, the reader may further comprise a reader board, wherein said strip reader and said controller are mounted on said reader board.

According to another aspect, the reader may further comprise an encryption board, wherein said encryption controller is mounted on said encryption board.

According to yet another aspect, said strip reader and said controller are mounted on said encryption board.

According to another aspect, the reader may further comprise a dongle, wherein the strip reader, the controller and the encryption controller are housed within a dongle.

According to yet another aspect, said dongle comprises a connector, said connector having a mechanical and pin layout that mechanically mates with an oximeter connector normally connected to a noninvasive optical sensor.

According to another aspect, said strip reader and said controller comprises an OEM strip reader and controller.

For purposes of summarizing the disclosure, certain aspects, advantages and novel features of the disclosure have been described herein. Of course, it is to be understood that not necessarily all such aspects, advantages or features will be embodied in any particular embodiment of the disclosure. Thus, the disclosures disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

The following drawings and the associated descriptions are provided to illustrate embodiments of the present disclosure and do not limit the scope of the claims.

DETAILED DESCRIPTION OF THE PREFERRED EMBODIMENTS

The present disclosure includes a pulse oximeter or other patient monitor as a minimally invasive glucometer. In an embodiment, a glucose strip reader is connected to, and/or in communication with, a pulse oximeter. The pulse oximeter is configured so that it acts as a minimally invasive glucometer when connected to the glucose strip reader, displaying glucose measurements to a user. For example, the user may first connect the strip reader to the pulse oximeter. Then, the user may insert a glucose strip in the strip reader. Next, the user may place a sample of their blood on the strip. The strip reader may then measure the glucose level of the user's blood and pass this information to the pulse oximeter. The pulse oximeter may then display the glucose level on the pulse oximeter display so that it may be read by the user. Thus, advantageously, according to various embodiments, the pulse oximeter or other patient monitor, when paired with the glucose strip reader, may additionally be used as a minimally invasive glucometer, among other things.

In an embodiment, communications between the glucose strip reader and the pulse oximeter or other patient monitor are encrypted. For example, the glucose strip reader may be authorized and/or authenticated to communicate with the pulse oximeter or other patient monitor.

To facilitate a complete understanding of the disclosure, the remainder of the detailed description describes the disclosure with reference to the drawings, wherein like reference numbers are referenced with like numerals throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

Figure 1:
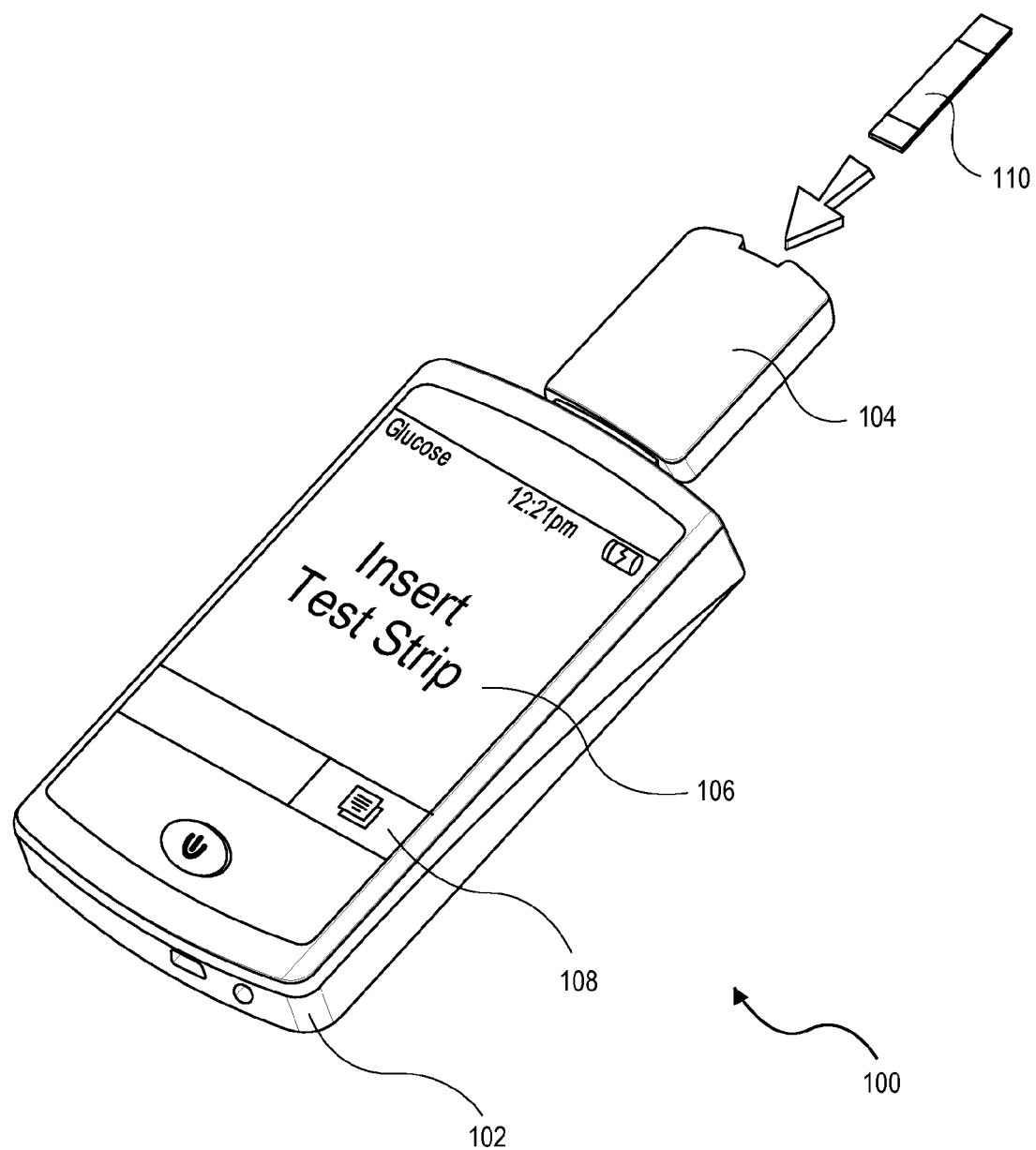
FIG. 1 illustrates an embodiment of a minimally invasive glucometer system.

FIG. 1 illustrates a minimally invasive glucometer system 100 according to an embodiment of the present disclosure, including a patient monitor 102 and a reader dongle 104. The system 100 interacts with disposable glucose strips 110, which in some embodiments, include source identifying strips and/or source identifying technology interacting with said dongle 104, and in other embodiments include straightforward commercially available disposable strips. Source identifying technology may advantageously include a chemical(s) recognizable by the reader and/or that cause the reader to generate output data recognizable by communicating processor. Other source identifying technology includes an electrical connection that reads, for example, a memory and/or electrical property of the strips 110, and/or RFID or other wireless based communication with the strip. Still other source identifying technology may include devices and/or chemicals associated with said strip that produce a recognizable signal when optically read by monitor 102. An artisan will recognize from the disclosure herein a number of technologies, protocols, and interactions that may provide source identification of the strips 110.

The patient monitor 102 comprises a display 106 and control buttons 108. Advantageously, in certain embodiments, the minimally invasive glucometer system 100 can have a shape and size that allows a user to operate it with a single hand, or attach it, for example, to a sleeve and/or other attachment mechanism proximate a patient's body or limb.

In the minimally invasive glucometer system 100, the patient monitor 102 may be connected to, and communicate with, the reader dongle 104. The patient monitor 102 may also communicate with the display 106 and the control buttons 108. Generally, blood or other solution is presented on the disposable glucose strip 110, and sample is inserted into reader dongle 104 where it is read by a reader designed to interact with the strip 110 (now carrying the sample).

In various embodiments, the user interacts with the minimally invasive glucometer system 100 to obtain spot check glucose measurements. As explained in more detail below with reference to FIGS. 2A-C and 3, in various embodiments the user inserts the disposable glucose strip 110 into the reader dongle 104, and then places a blood sample on the disposable glucose strip 110. The minimally invasive glucometer system 100 may then display glucose measurements obtained from reader dongle 104. Advantageously, the patient monitor 102 may be used, according to various embodiments, as a minimally invasive glucometer as it displays glucose measurements obtained from the reader dongle 104.

In an embodiment, the patient monitor 102 comprises a commercial available monitor from, for example, Masimo Corporation. For example, the patient monitor 102 may comprise any of Rad-8®, Rad-5®, Rad®-5v, SatShare®, Radical7™, Rad87™, Rad57™ monitors, or Pronto or Pronto-7 spot check monitors.

Figure 2A:
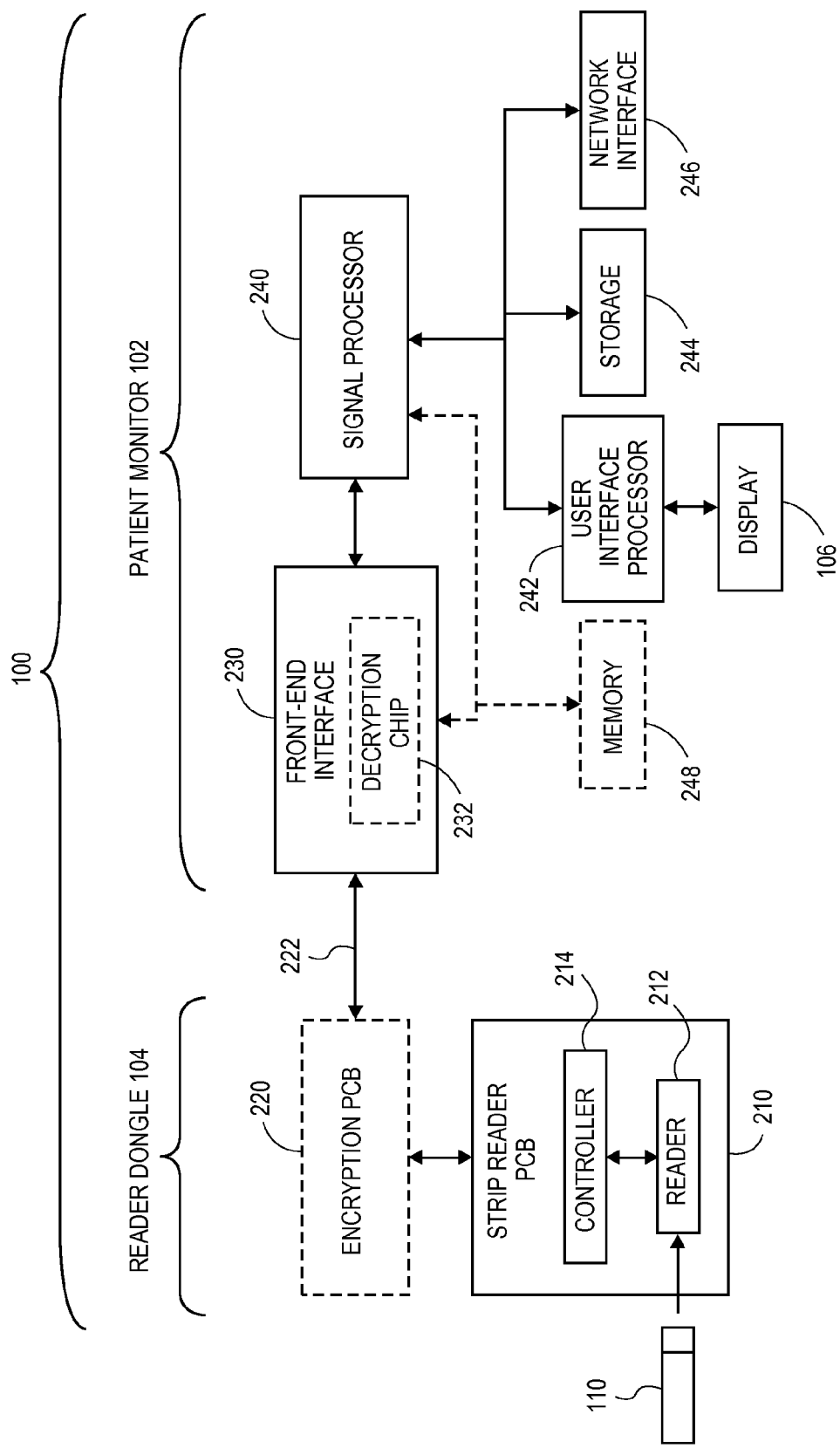
FIG. 2A illustrates a simplified block diagram of an embodiment of a minimally invasive glucometer.

FIG. 2A illustrates a simplified exemplary block diagram of an embodiment of the minimally invasive glucometer system 100 described above with reference to FIG. 1. According to an embodiment, the minimally invasive glucometer system 100 includes the reader dongle 104, the patient monitor 102, and an optionally encrypted communications link 222. The reader dongle 104 may include a strip reader printed circuit board (PCB) 210 and an optional encryption PCB 220 (also referred to as an encryption board). Additionally, the strip reader PCB 210 (also referred to as a reader board) may include a reader 212 and a controller 214. The patient monitor 102 may include a front-end interface 230, a signal processor 240, a user interface processor 242, a display 243, a storage 244, a network interface 246, and/or an optional memory 248. The front-end interface 230 may further include an optional decryption chip 232. In an embodiment, the optional encryption PCB 220 includes an encryption chip, an encryption controller, and/or an encryption microcontroller (as described below in referenced to FIG. 2B). Other embodiments may include other arrangements of the hardware components, one or more other boards, flexible circuits, and/or the like, or even be incorporated into one or more controllers, microprocessors or the like, and are still within the scope of the present disclosure. For example, in an embodiment, each of the controller 214, the reader 212, and an encryption controller may be mounted on the same board.

In the minimally invasive glucometer system 100, the strip reader PCB 210 may include the reader 212 and the controller 214 in communication with each other. Further, the strip reader PCB 210 and the optional encryption PCB 220 of the reader dongle 104 may be in communication with each other. The optional encryption PCB 220 of the reader dongle 104 may be in communication with the front-end interface 230 of the patient monitor 102. Communications from the optional encryption PCB 220 and the front-end interface 230 may occur over the optionally encrypted communications link 222. The front-end interface 230 may contain the optional decryption chip 232, and may be in communication with the optional decryption chip 232. Within the patient monitor 102, the front-end interface 230 may be in communication with the signal processor 240, which may be in communication with the user interface processor 242, the storage 244 and/or the network interface 246. Further, the optional memory 248 may be in communication with the front-end interface 230 and the signal processor 240, and the user interface processor 242 may be in communication with the display 243.

In operation, according to an embodiment the disposable glucose strip 110 is inserted into strip reader PCB 210, and read by reader 212. Minimally invasive glucose measurements (also referred to as glucose level(s)) may be obtained from the disposable glucose strip 110 by controller 214. Glucose measurement data may then be forwarded by strip reader PCB 210 to the optional encryption PCB 220. The optional encryption PCB 220 may encrypt the minimally invasive glucose measurement data so that they may then be communicated to the patient monitor 102. The encrypted glucose measurement data may then be transmitted to the front-end interface 230 over the optionally encrypted communications link 222. Communications over the optionally encrypted communications link 222 may be through wired and/or wireless connections, and may use any suitable communications protocol. For example, communication may be serial or parallel, through Universal Serial Bus (USB) (wired or wireless), Ethernet, Bluetooth, Near Field Communications (NFC), radio frequency (RF), infrared, and/or WiFi (such as any 802.1x interface), among others as is known in the art. In an embodiment, the strip reader PCB 210 may be referred to as a minimally invasive glucose reader. In another embodiment, the reader 212 may be referred to as a minimally invasive glucose reader.

According to an embodiment the front-end interface 230 provides an interface that decrypts and adapts the output of the optional encryption PCB 220. For example, in an embodiment, the optional decryption chip 232 decrypts the glucose measurement data transmitted to the front-end interface 230 so that the data may be processed by signal processor 240. Advantageously, the optional encryption PCB 220 and the optional decryption chip 232 may allow for encrypted communications to ensure that the reader dongle 104 is compatible with, and authorized for use with, the patient monitor 102. In an embodiment, the optional decryption chip 232 prevents communication with the reader dongle 104 until the optional encryption PCB 220 is authenticated as having the proper credentials to communicate with the patient monitor 102. The optional encryption PCB 220 and the optional decryption chip 232 may implement any suitable cryptographic system, for example public/private key, among others. In an alternative embodiment, the minimally invasive glucometer system 100 does not include the optional encryption PCB 220 and the optional decryption chip 232. In this embodiment, the strip reader PCB 210 may communicate directly with the front-end interface 230, and the optionally encrypted communications link 222 may transmit unencrypted data.

The decrypted glucose measurement data may then be transmitted to the signal processor 240. In an embodiment, the signal processor 240 may include processing logic that determines measurements for desired analytes, such as glucose, based on the signals received from the reader dongle 104. The signal processor 240 may be implemented using one or more microprocessors or subprocessors (e.g., cores), digital signal processors, application specific integrated circuits (ASICs), field programmable gate arrays (FPGAs), combinations of the same, and/or the like.

The signal processor 240 may provide various signals that control the operation of strip reader PCB 210. For example, the signal processor 240 may provide signals to reset the strip reader PCB 210, and/or direct the strip reader PCB 210 to begin reading and transmitting glucose measurement data. As also shown, an optional memory 248 may be included in the front-end interface 230 and/or in the signal processor 240. This optional memory 248 may serve as a buffer and/or storage location for the front-end interface 230 and/or in the signal processor 240, among other uses. Moreover, the monitor 102 may power one or more of the PCBs 210, 220.

The user interface processor 242 may provide an output, for example the display 106 (see also FIG. 1), for presentation to the user of the minimally invasive glucometer system 100. The user interface processor 242 may be implemented to include and/or communicate with a touchscreen display, an LCD display, an organic LED display, or the like. The signal processor 240 may transmit minimally invasive glucose measurement information to the user interface processor 242 such that the information may then be displayed on the display 106, which may then be observed by the user. Additionally, the user may provide inputs to the user interface processor 242 through, for example, the control buttons 108 on the display 106. User inputs may be processed by the user interface processor 242 and then transmitted to the signal processor 240, where they may be processed and may, for example, control the reader dongle 104. For example, the user may turn the reader dongle 104 and/or the patient monitor 102 on and off. Alternatively, as another example, the user may use the control buttons 108 to direct the strip reader PCB 210 to read the disposable glucose strip 110 and transmit the minimally invasive glucose measurements to the signal processor 240, and subsequently to the display 106 where they may be observed by the user.

The storage 244 and the network interface 246 represent other optional output connections that may be included in the patient monitor 102. The storage 244 may include any computer-readable medium, such as a memory device, hard disk storage, EEPROM, flash drive, or the like. The various software and/or firmware applications may be stored in the storage 244, which may be executed by the signal processor 240 and/or another processor of the patient monitor 102. The network interface 246 may be a serial bus port (RS-232/RS-485), a Universal Serial Bus (USB) port, an Ethernet port, a wireless interface (for example, WiFi such as any 802.1x interface, including an internal wireless card), and/or other suitable communication device(s) that allows the patient monitor 102 to communicate and share data with other devices. The patient monitor 102 may also include various other components not shown, such as a microprocessor, graphics processor, and/or controller to output to the user interface processor 242, to control data communications, to compute data trending, and/or to perform other operations. Alternatively, the patient monitor 102 may not include the user interface processor 242, but may communicate user interface data directly between the signal processor 240 and the display 106.

In an embodiment, the strip reader PCB 210 comprises a commercially available OEM strip reader from, for example, Nova Medical, or others. In an embodiment, the strip reader PCB 210 comprises a prick reader that operates by pricking the user's fingertip or other area of their body to obtain a blood sample to be analyzed. In this embodiment, the disposable glucose strip 110 may not be necessary for operation of the minimally invasive glucometer system 100.

In an embodiment, the optional encryption PCB 220 may be packaged together with the strip reader PCB 210 in the reader dongle 104. Alternatively, the optional encryption PCB 220 may be packaged separately, and may include an external connection for communication with the strip reader PCB 210 and the patient monitor 102. In another alternative, strip reader PCB 210 communicates wirelessly (such as through WiFi or other suitable communications protocol) with the optional encryption PCB 220 and/or the patient monitor 102.

In an embodiment, the optional encryption PCB 220 may not be a PCB, but may be embodied in a separate chip, ASIC, FPGA, or the like, or may alternatively be integrated with the strip reader PCB 210. Alternatively, the functionality of the optional encryption PCB 220 may be accomplished in a software application running on a multipurpose processor.

Alternatively, as mentioned above, in an embodiment the minimally invasive glucometer system 100 may not include the optional encryption PCB 220 and the optional decryption chip 232, so that communications between the strip reader PCB 210 and the patient monitor 102 do not include encryption and decryption of glucose measurement data. In this embodiment, the reader dongle 104 comprises the strip reader PCB 210.

The strip reader PCB 210 may also be referred to as a strip reader, a glucose reader, a minimally invasive glucose reader, and/or a blood glucose reader, among other things. Thus, in embodiments in which the optional encryption PCB 220 is not included in the reader dongle 104, references a reader dongle, strip reader, glucose reader, minimally invasive glucose reader, and/or blood glucose reader may be understood to reference the strip reader PCB 210. Additionally, it is to be understood that in some embodiments the reader dongle 104 may or may not include the optional encryption PCB 220. Thus in some embodiments references to the reader dongle 104 may or may not include the optional encryption PCB 220.

In further embodiments, the monitor 102 receives a signal that the PCB 210 (and optionally, PCB 220) is present, thereby allowing the monitor 102 to change programming from an oximeter to programming as disclosed herein. In an embodiment, the mechanical connection of the PCB 210 (and optionally, PCB 220) signals the monitor 102 that it is to configure itself as a minimally invasive glucometer. In other embodiments, receipt of communication from the PCB 210 (and optionally, PCB 220) signals the monitor 102 that it is to configure itself as a minimally invasive glucometer. In still other embodiments, the monitor 102 is configured to determine that it is not receiving optical data from a non-invasive optical sensor, but is receiving other data, and one possible source of the other data is the PCB 210 (and optionally, PCB 220), and therefore, upon detecting said other data, the monitor 102 configures itself as a minimally invasive glucometer. In other embodiments, the PCB 210 (and optionally, PCB 220) includes some or all of the software needed to execute a minimally invasive glucometer and the monitor 102 receives this software and then executes its processes to implement said glucometer functions.

Although disclosed with reference to the specific embodiments of FIGS. 1 and 2, an artisan will recognize from the disclosure herein other hardware and/or software configurations for accomplishing the desired functionality, including, for example, custom semiconductors, controllers, processors, or the like for performing individual or sets of functions.

Figure 2B:
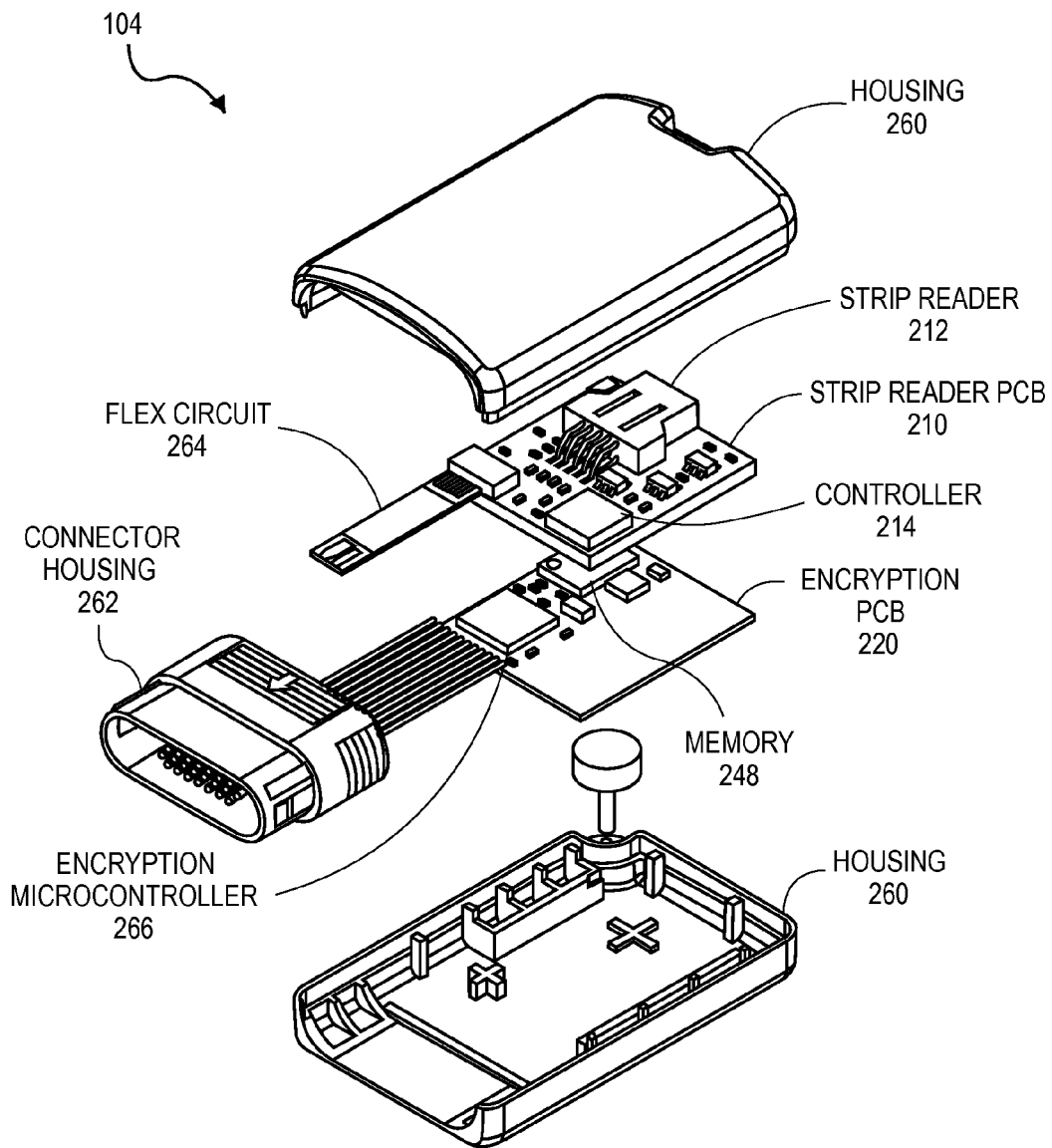
FIG. 2B illustrates an exploded view of an embodiment of a reader dongle that may be used with the minimally invasive glucometer.

FIG. 2B illustrates an exploded view of an embodiment of the reader dongle 104 that may be used with the minimally invasive glucometer. Further, FIG. 2C illustrates a perspective view of an embodiment of the fully assembled reader dongle 104 of FIG. 2B.

Figure 2C:
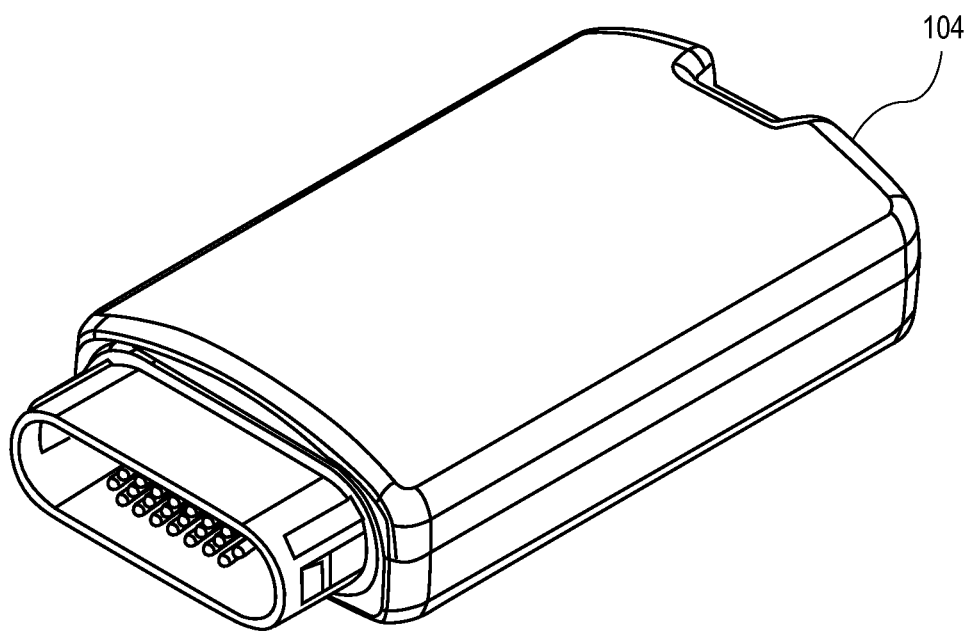
FIG. 2C illustrates a perspective view of an embodiment of the reader dongle of FIG. 2B that may be used in a minimally invasive glucometer.

The embodiment of the reader dongle 104 shown in FIGS. 2B and 2C includes a housing 260, a connector housing 262, the strip reader PCB 210 (as described in reference to FIG. 2A), and the optional encryption PCB 220 (as described in reference to FIG. 2A). Further, as described with reference to FIG. 2A above, the strip reader PCB 210 includes the strip reader 212, and the controller 214. Also shown in FIG. 2B is a flex circuit 264 which may be used to connect the strip reader PCB 210 to the optional encryption PCB 220. The optional encryption PCB 220 also includes the optional memory 248 (as described above in reference to FIG. 2A), and an encryption microcontroller 266.

In operation, according to various embodiments and as described above with reference to FIG. 2A, the strip reader PCB 210 communicates measurements to the optional encryption PCB 220 through the flex circuit 264. The flex circuit 264 may act as a connector to enable communications between the two PCBs. Once measurements are communicated to the optional encryption PCB 220, the encryption microcontroller 266 may, as described above, encrypt the data, thus enabling encrypted communication with the patient monitor 102. In various embodiments, the encryption microcontroller 266 may comprise an encryption chip, an encryption controller, an encryption microcontroller, and/or any combination of encryption chips, controllers, and microcontrollers. In an embodiment, the strip reader PCB 210 cannot communicate with the patient monitor 102 directly, as the strip reader PCB 210 lacks devices or modules to encrypt the communications. Thus, the encryption microcontroller 266 may encrypt communications originating with the reader dongle 104 and transmitting to the front-end interface 230 of the patient monitor 102. Thus, in an embodiment, only the optional encryption PCB 220 may communicate with the patient monitor 102 via encrypted communications. The encryption microcontroller 226 advantageously provides, according to various embodiments, quality control by limiting the type and suppliers of strip reader technology that can communicate with a specific manufacture's instruments, such as, for example, the monitor 102. Quality control may be advantageous as the instrument manufacturer is aware of tolerances, accuracies, requirements, and/or other characteristics often used during technology development and deployment to consumers and/or caregivers.

In the reader dongle 104 of the embodiments of FIGS. 2B and 2C, the connector housing 262 houses an electrical connector that may be coupled to the patient monitor 102, as shown in FIG. 1. The connector type of the connector housing 262 may include any suitable connector for allowing communications between the reader dongle 104 and the patient monitor 102. In an embodiment, the connector housing 262 may securely couple the reader dongle 104 to the patient monitor 102 such that the two are affixed or coupled to one another. In an embodiment, the connector housing 262 may comprise a flexible connection and/or a hinged connection. In an embodiment, the reader dongle 104 does not include a connector housing 262, but rather communications between the reader dongle 104 and the patient monitor 102 are wirelessly transmitted. In still other embodiments, a flexible circuit and/or cable could extend between the dongle 104 and the connector end thereof allowing placement of the dongle in a convenient location. Other embodiments may also include a mechanical latch and/or catch to securely hold the housing 262 or at least the connector portion thereof to the monitor 102. Some embodiments, may include a mechanical and pin layout that mechanically mates the connector housing 262 with the pulse oximeter 102.

Figure 3:
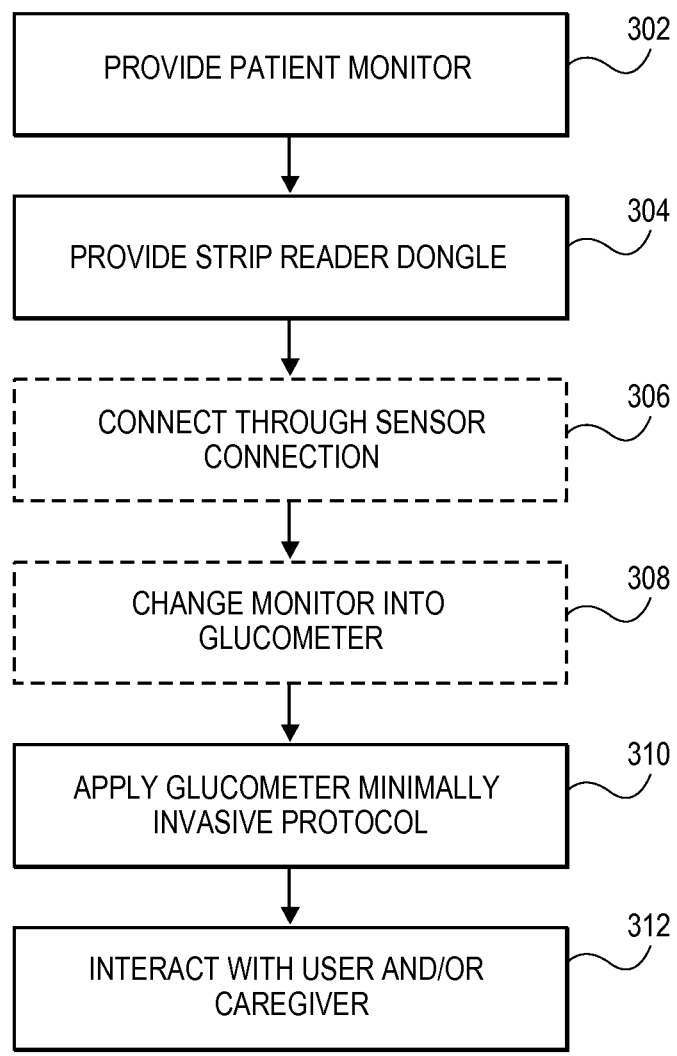
FIG. 3 illustrates a simplified configuration process of an embodiment of a minimally invasive glucometer.

FIG. 3 illustrates am example simplified configuration process of an embodiment of a minimally invasive glucometer. In various embodiments the configuration process may include more of fewer blocks, and/or the blocks may be arranged in a different order. The exemplary configuration process begins at block 302 wherein a patient monitor, such as the patient monitor 102, is provided. Next, in block 304, a strip reader dongle, such as the reader dongle 104, is provided.

Then, in optional block 306, the strip reader dongle is connected to the patient monitor 102 through a sensor connection. The sensor connection is typically associated with a sensor connector for an optical sensor used in oximetry and known to an artisan from the disclosure herein. Once connected, the data can be transmitted between the strip reader dongle 104 and the patient monitor 102. The sensor connection may be, for example, a port, plug, and/or jack on the side of the patient monitor. In an embodiment, the strip reader dongle is a single self-contained unit that may be physically and securely attached to the sensor connection of the patient monitor (see, for example, the illustration of an embodiment of the minimally invasive glucometer system 100 in FIG. 1, and/or FIG. 7B). Such an embodiment has the advantages of providing structural support to the strip reader dongle and clearly indicating to a user of the minimally invasive glucometer system 100 when the strip reader dongle is connected to the patient monitor. In another embodiment, the strip reader dongle may include a cable and/or cord that physically connects to the sensor connection of the patient monitor (see, for example, the illustration of a corded strip reader dongle connecting to an patient monitor in FIG. 7A).

Additionally, in block 306 the strip reader dongle may be authenticated and/or authorized by the patient monitor, as described above in reference to FIG. 2A. If the strip reader dongle is not authenticated and/or authorized, and/or the strip reader dongle is not compatible with the patient monitor, the user may be notified. For example, the user may be presented with the display of FIG. 7C. Alternatively, the authentication and/or authorization of the strip reader dongle may be accomplished in block 310 of FIG. 3.

In an embodiment, optional block 306 is not included in the configuration process. In this embodiment, the strip reader dongle is not physically connected to the patient monitor, but communication (in other words, data transmission) between the strip reader dongle and the patient monitor occurs wirelessly. Such wireless communications may be accomplished in any of the ways described above in reference to FIG. 2A and the optionally encrypted communications link 222. Alternatively, the strip reader dongle may be physically attached to the patient monitor, but communications may occur wirelessly.

Continuing to optional block 308, the patient monitor is changed into a glucometer. This may be accomplished, for example, by displaying the blood glucose measurement results on the display of the patient monitor (as described above with respect to the FIG. 2A). The patient monitor may automatically detect communications with, or the connection to, the strip reader dongle. In addition to detection methods discussed in the foregoing, the monitor may advantageously include an RFID reader that receives a signal when the dongle is within a proximity to the monitor and/or other detection methods an artisan would recognize after reviewing the disclosure herein.

Upon detecting the strip reader dongle, the patient monitor may, for example, update a user interface to include instructions and controls relevant to use of the patient monitor as a minimally invasive glucometer, begin communications with the strip reader dongle, authenticate the strip reader dongle, and/or begin quality control checks with the strip reader dongle, among other things. Alternatively, a user of the minimally invasive glucometer system may manually prompt the patient monitor to change to a glucometer.

In another embodiment, the patient monitor is not changed into a glucometer, but functions as a display in communication with an external glucometer. In this embodiment, the strip reader dongle may include additional processors and memory, among other things, for calculating blood glucose levels and displaying those levels. The data may then be transmitted to the patient monitor and displayed to the user.

In an embodiment, the patient monitor may be used for functions other than a glucometer while the strip reader dongle is attached to, or in communication with, the patient monitor. For example, the patient monitor may be used simultaneously, or at separate times, as a glucometer and a pulse oximeter, among other things. Thus, advantageously, according to various embodiments, the patient monitor provides additional functionality and patient monitoring abilities to the user.

At block 310 a glucometer minimally invasive protocol is applied. At this point, the patient monitor may function at least in part as a minimally invasive glucometer, interfacing and/or communicating with the strip reader dongle. For example, in this block the strip reader dongle may be authorized and/or authenticated, communication and/or transmission integrity checks may be performed, and/or the display of the patient monitor may display information relevant to performing a minimally invasive glucose test, among other things.

Then, in block 312, the minimally invasive glucometer system, now including the patient monitor and the strip reader dongle in communication with one another, interacts with the user and/or a caregiver. As described above, and as further described below, it is at this point that the user/caregiver may be directed by the minimally invasive glucometer system to, for example, insert a test strip into the strip reader dongle, apply blood to the test strip, and/or read the output of the glucometer measurement. Additionally, the user/caregiver may be instructed to perform a quality control test and/or linearity control test to ensure the results of the glucometer measurement are accurate.

In an embodiment, the strip reader dongle may alternatively be a prick reader dongle that operates by pricking the user's fingertip, or other area of the user's body, to obtain a blood sample to be analyzed.

In general, in some embodiments, the patient monitor or pulse oximeter of the minimally invasive glucometer system continue to function in their respective roles a patient monitor or pulse oximeter, and not exclusively as glucometers. Thus, for example, the patient monitor 102 may continue reading blood oxygenation and pulse rate, while also functioning as a minimally invasive glucometer. In other embodiments, the patient monitor or pulse oximeter of the minimally invasive glucometer system may function exclusively, semi-exclusively, periodically, and/or only for a time, as a minimally invasive glucometer.

Figure 4B:
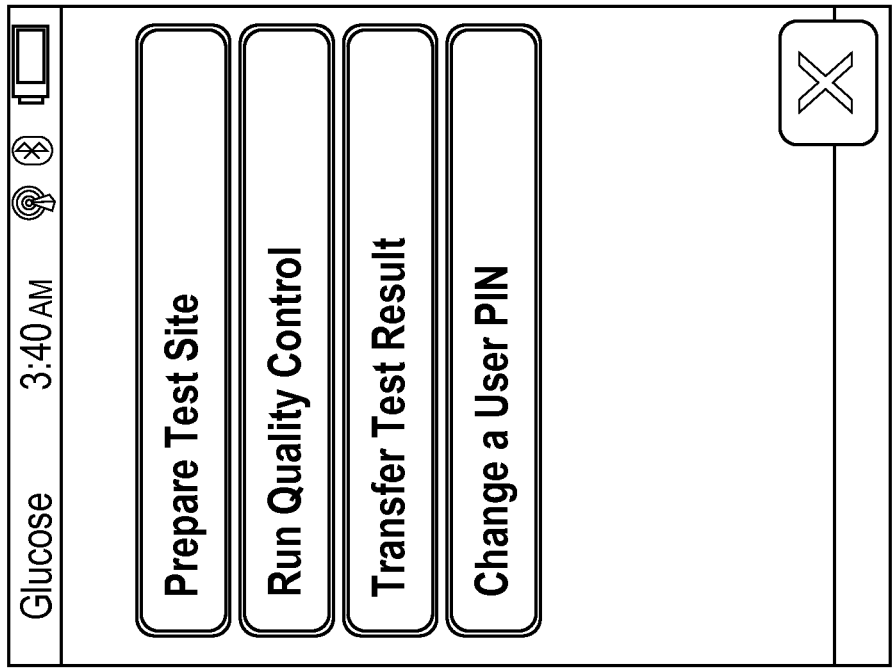
FIGS. 4A-4T illustrate exemplary user interfaces of a minimally invasive glucometer according to various embodiments of the present disclosure.
Figure 4A:
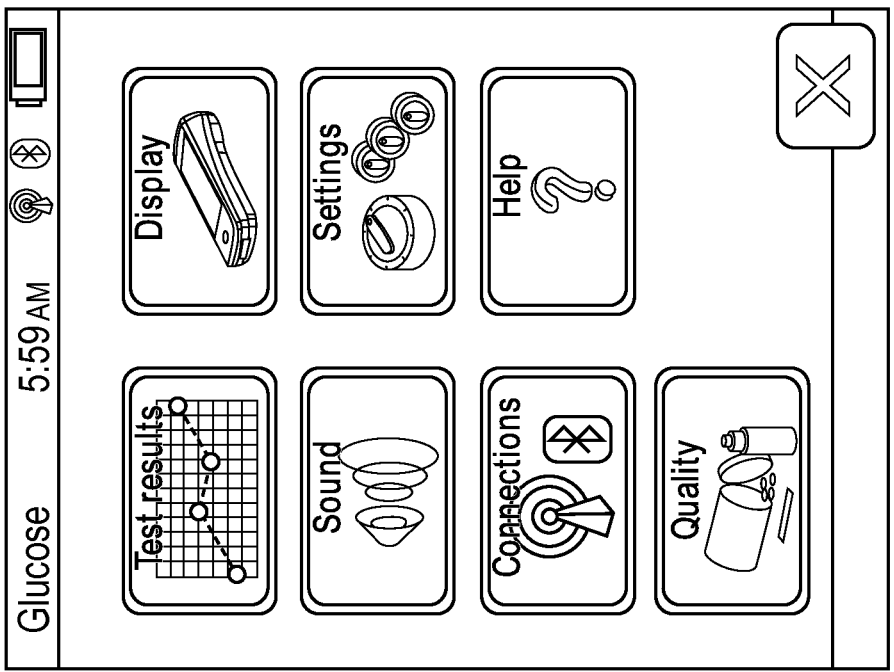
Figure 4D:
Figure 4C:
Figure 4F:
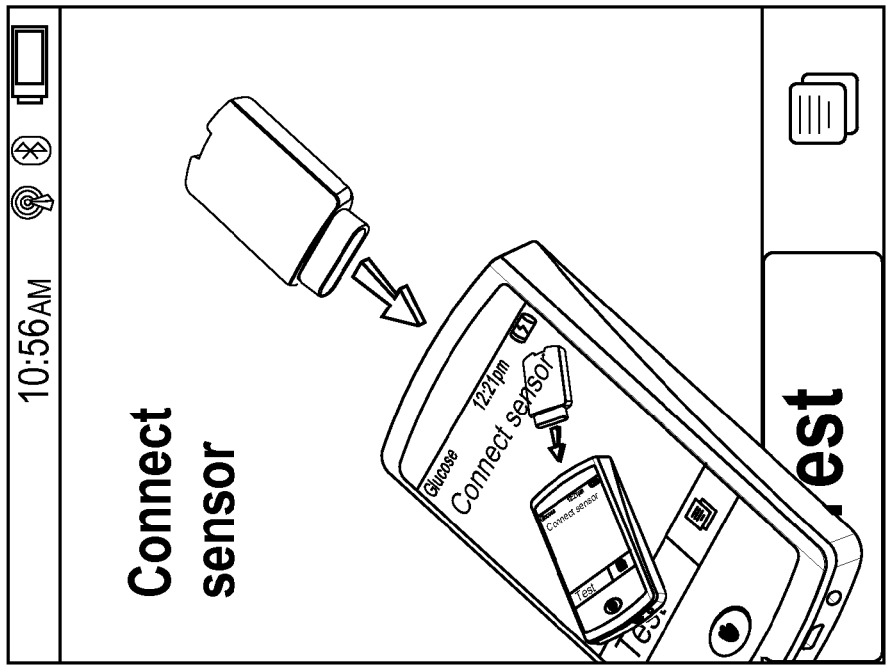
Figure 4E:
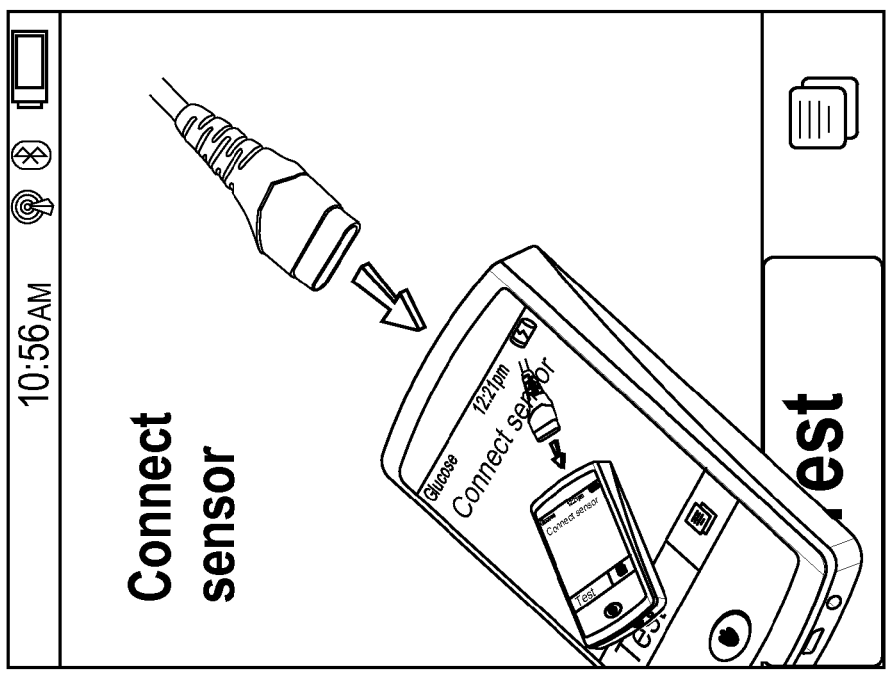
Figure 4H:
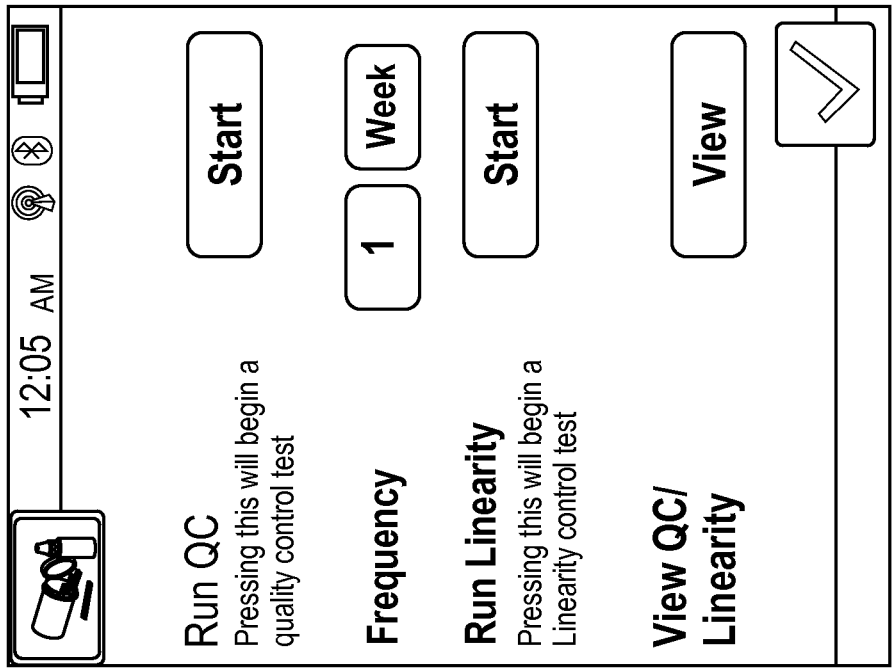
Figure 4G:
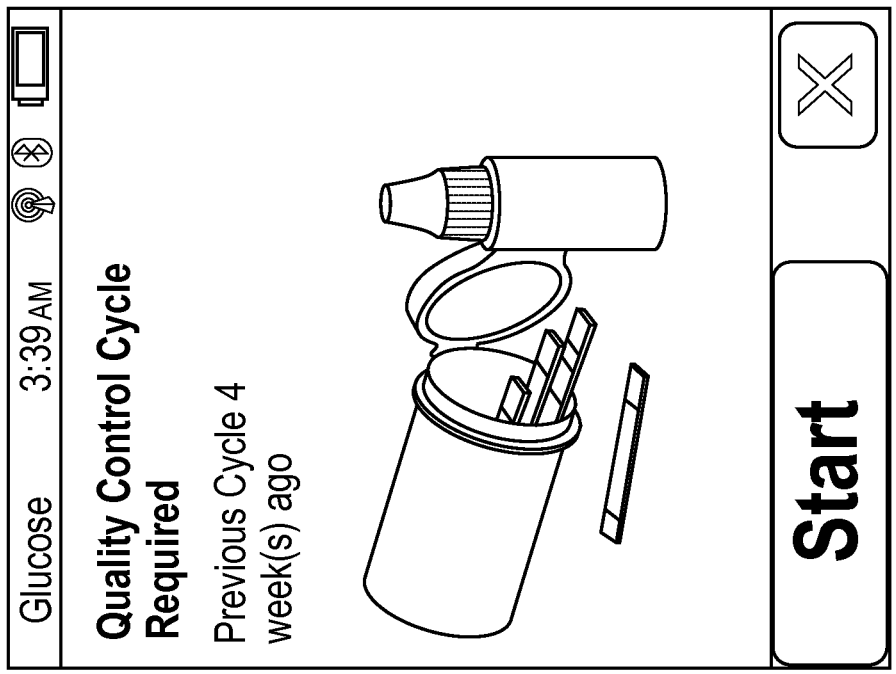
Figure 4J:
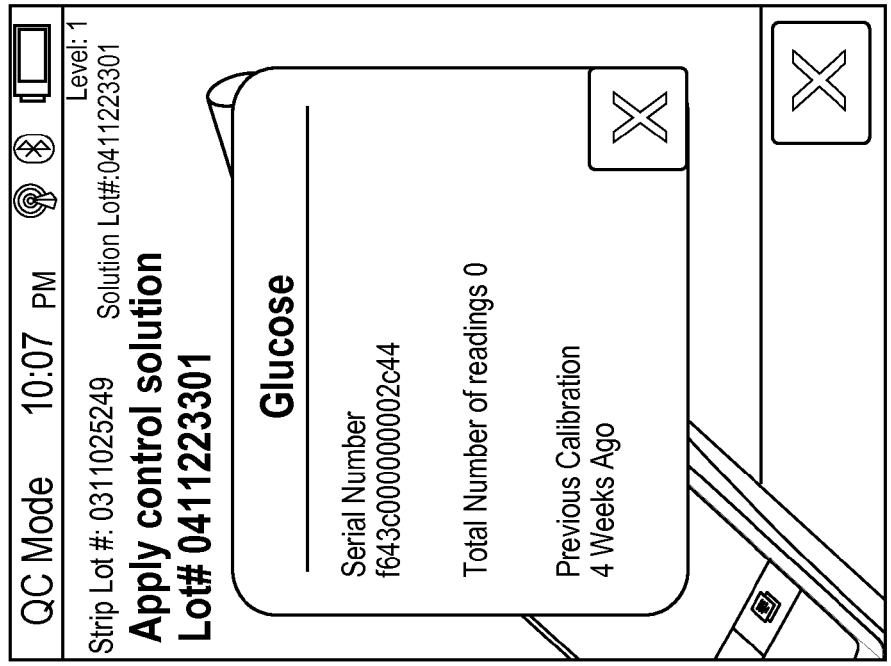
Figure 4I:
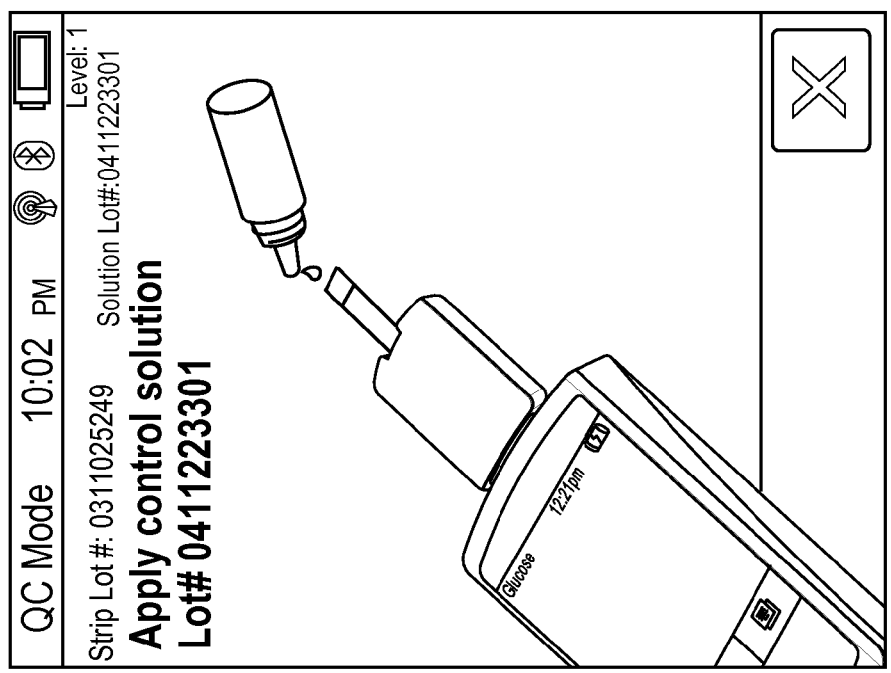
Figure 4L:
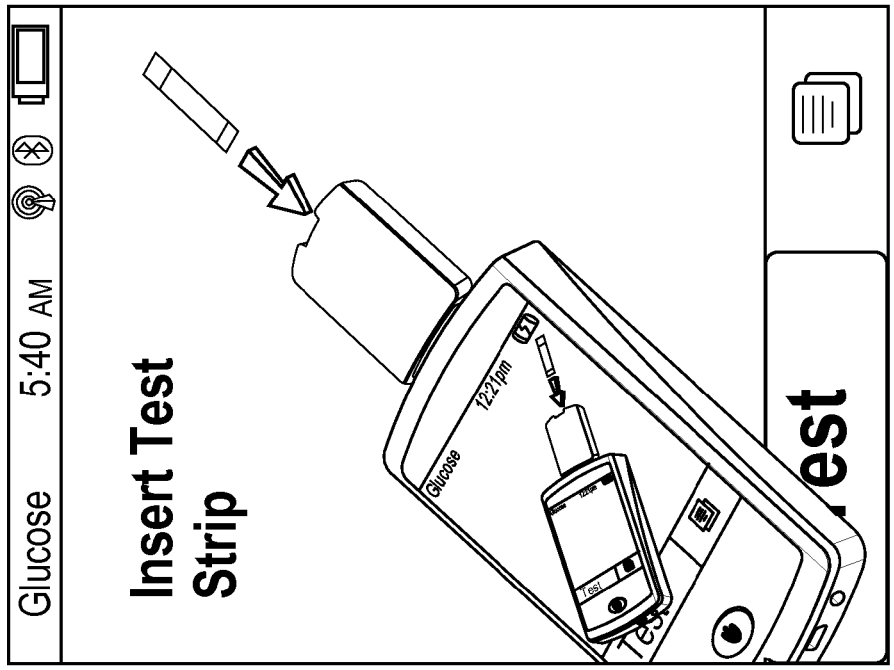
Figure 4K:
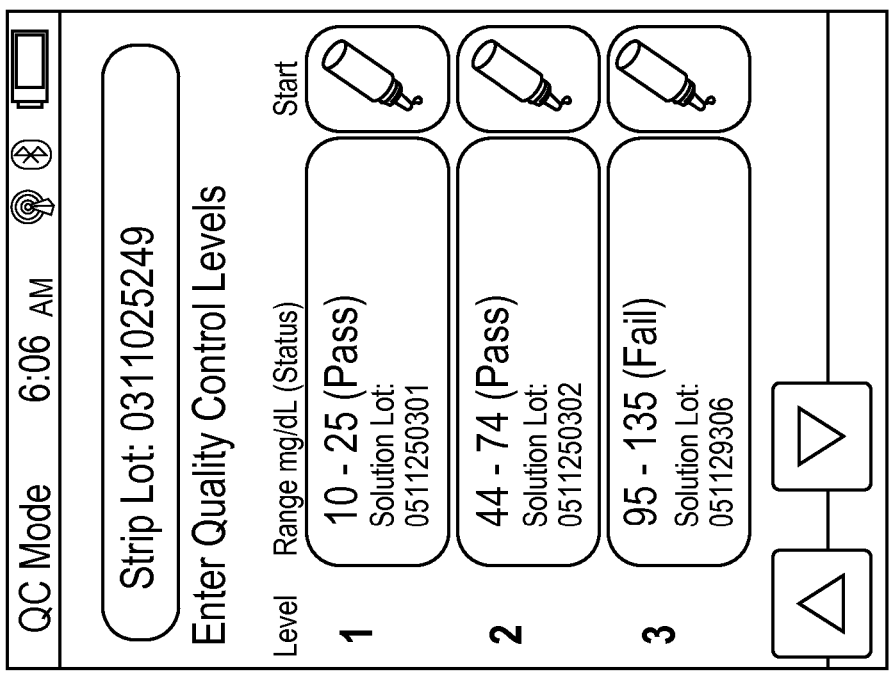
Figure 4N:
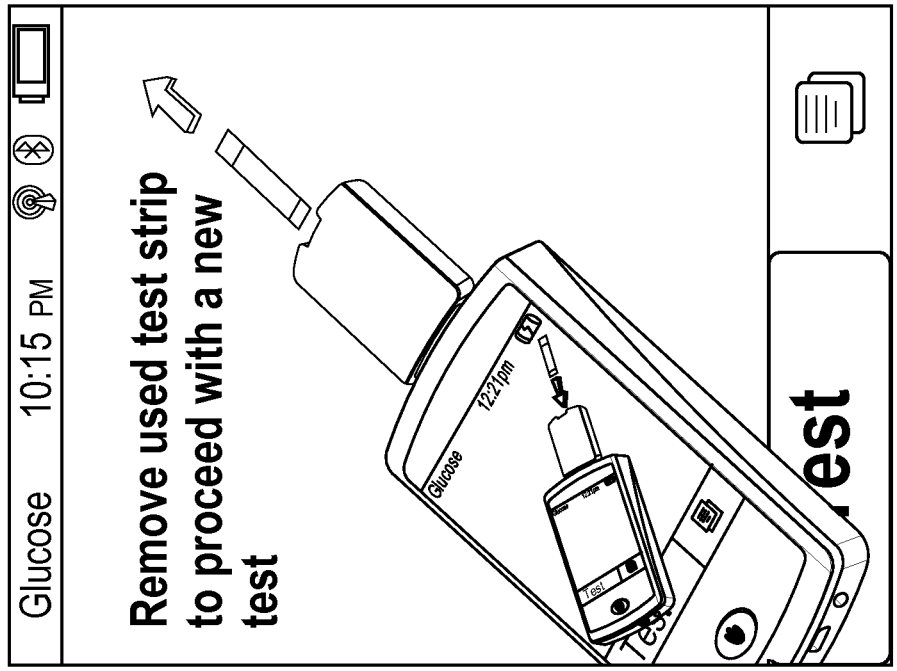
Figure 4M:
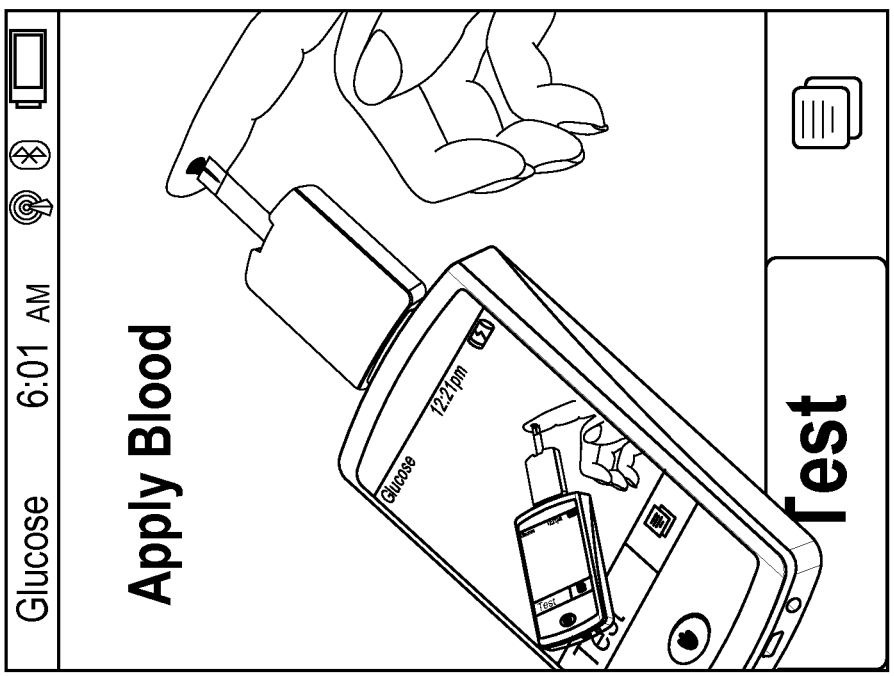
Figure 4P:
Figure 4O:
Figures 4Q, 4R:
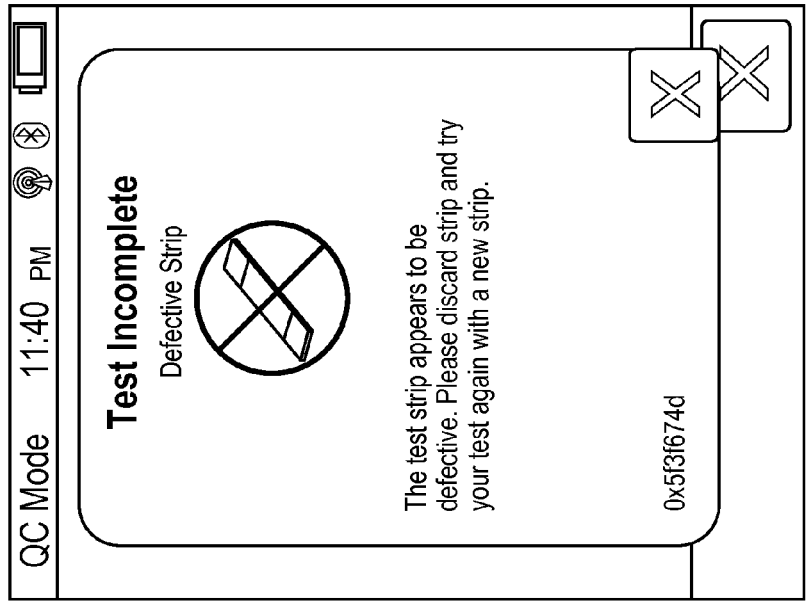
Figure 4T:
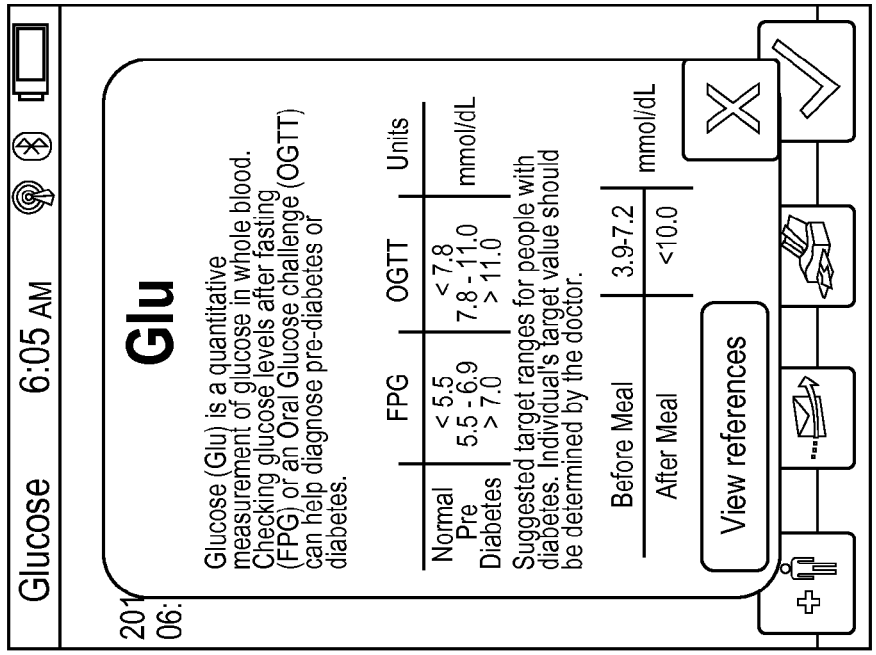
Figure 4S:
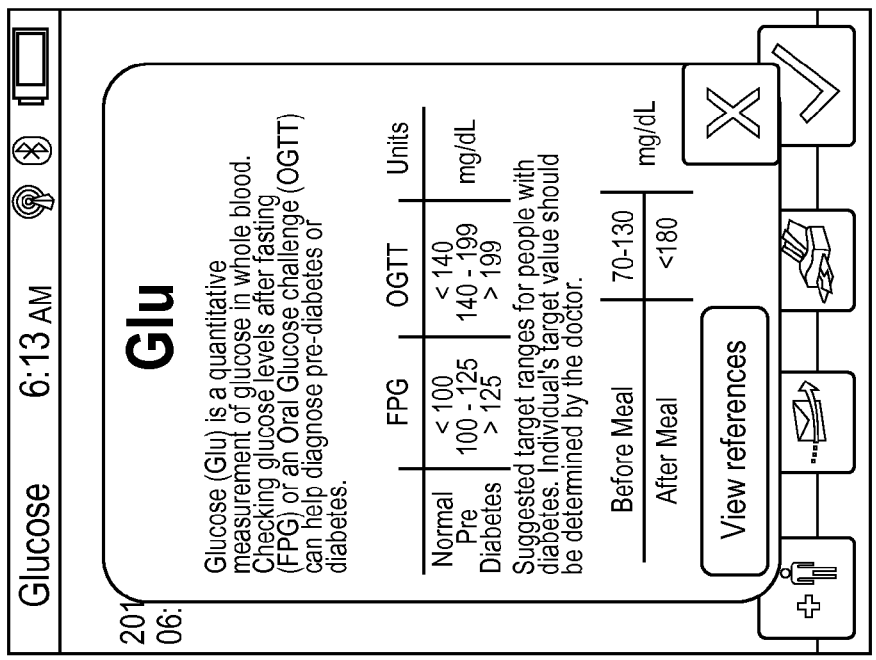

FIGS. 4A-4S illustrate exemplary user interfaces of the minimally invasive glucometer system 100 of FIG. 1, according to various embodiments of the present disclosure. In an embodiment, various of the example user interfaces of FIGS. 4A-4S may be displayed, for example, in response to the strip reader dongle being connected to, or brought into communication with, the patient monitor such that the patient monitor functions, at least in part, as a minimally invasive glucometer. As described above, the various user interfaces may be shown on a display of the minimally invasive glucometer system. The various user interface may be shown, for example, as a user of the minimally invasive glucometer system performs various functions and/or otherwise interacts with the system, as described in detail below. Further, as described above, the system may include one or more buttons, and/or the display of the system may be a touch-sensitive display such that a user may interact with, and/or select, various aspects of the system direct via the touch-sensitive display.

FIGS. 4A-4D illustrate exemplary settings user interfaces of the system. For example, in the various user interfaces a user of the minimally invasive glucometer system may select to perform a glucose test, read test results, adjust various settings, perform a quality control of the system, transfer test results (for example, to another device or computer system), set and/or view patient-related information, and/or view help information. In an embodiment the user may select the operating and/or test mode of the minimally invasive glucometer system 100. In an embodiment, the minimally invasive glucometer system 100 may be set to a maximum sensitivity mode, a normal sensitivity mode, or a multi mode. The operating mode may be selected by the user before the measurement process begins. The user may be prompted with instructions for the selected mode. For example, in normal sensitivity mode, a true parameter value is estimated by providing a predicted parameter value based on a measured set of input values. This mode can be useful where a quick estimate of a predicted parameter value is needed. In maximum sensitivity mode (max mode), more accurate results may be obtained. In multi mode, successive measurements may be taken. For example, three separate input values may be measured, and the sensor may be reapplied between measurements. A predicted parameter value may be calculated for each of the measured input values. Optionally, one or more of the predicted parameter values may be dropped and the remaining values may be averaged to yield a final prediction. For example, of three predicted parameter values, the median value may be averaged with the next closest value and provided to the user. The multi-mode may provide a more accurate measurement with a higher confidence than the normal mode and/or the max mode. Additional examples of systems and processes of multiple parameter measurements may be found in at least U.S. patent application Ser. No. 13/548,637, filed Jul. 13, 2012, and entitled "MULTIPLE MEASUREMENT MODE IN A PHYSIOLOGICAL SENSOR" (now published as U.S. Patent Application Publication No. 2013/0041591), which application is hereby incorporated by reference herein in its entirety and for all purposes.

In an embodiment, the user may interact with the user interface to take various actions with respect to results of minimally invasive glucose tests that have been performed. For example, the user may email test results, to for example, their physician. The user may also optionally print the test results, and/or export the test results to, for example, an external memory such as a MicroSD card. The user may also delete the test results.

In various embodiments the system may include various patient information interfaces. For example, via a user interface the user may input their user id, patient id, birthday, and gender. In another example, via the user interface of FIG. 4D, the user (for example, a patient) may set and/or view various patient information and/or patient/user preferences. For example, the user/patient may set a height and weight, may add notes, and/or may designate a test digit (for example, a particular finger or fingers from which blood will be taken for the minimally invasive glucose test). The minimally invasive glucometer system 100 may thus, for example, record and/or track from which finger the blood is obtained on each blood glucose reading, and/or may instruct the user on which finger to use.

FIGS. 4D-4E illustrate exemplary reader dongle connection interfaces. For example, in an embodiment, in FIG. 4D, the user is instructed to attach the reader dongle 104 to the patient monitor 102. In this embodiment, the reader dongle 104 includes a cord that attaches to the patient monitor 102, in this example, a Masimo Pronto-7 spot check monitor. In another embodiment, in FIG. 4E, the reader dongle 104 is a self-contained unit that plugs into the patient monitor 102. In an embodiment the system may include an interface notifying the user when an incompatible reader dongle 104 has been attached to the patient monitor 102. Such an interface may be presented to the user when, for example, the front-end interface 230 of FIG. 2A indicates that the reader dongle 104 does not have the correct optional encryption PCB 220, the reader dongle 104 is incompatible with the patient monitor 102, the reader dongle 104 cannot be authenticated, and/or the reader dongle 104 is not authorized to interface with the patient monitor 102.

The system may further include, in various embodiments, various quality control and/or quality control test user interfaces. For example, FIGS. 4G-4K illustrate various example quality control test user interfaces. In an embodiment, the minimally invasive glucometer system 100 runs quality control cycles periodically to ensure that proper measurements are being obtained from the strip reader PCB 210. In an embodiment, the system may instruct the user to run a quality control cycle when needed and/or according to a schedule (for example, as shown in FIG. 4G). Further, as shown in FIG. 4H, the user may manually initiate quality control and/or linearity control cycles, may set a frequency with which quality control cycles run, and/or may view quality control and/or linearity control cycle results. When a quality control cycle is run, the user may be instructed by the minimally invasive glucometer system 100 to insert a test strip, apply a control solution (for example, as shown in FIG. 4I), and/or run a test. In an embodiment, the user may view various details related to the quality control of the system, for example as shown in the user interface of FIG. 4J. Additionally, as shown in the example user interface of FIG. 4K, the user may be give an indication of a pass or a fail of a quality control text. As shown, a quality control test/cycle may include testing multiple control solutions with particular strip lots. In an embodiment, passing all quality control and/or linearity tests may be required before a glucose test may be run. In an embodiment, three tests are run for each quality control cycle. For example, often strip reader manufacturers provide solutions for testing strip readers. The user drips solution onto a test strip and inserts the strip into the reader. The solution is designed to cause the reader, when functioning properly, to provide a measurement within a provided range of acceptable measurements. These solutions may include three bottles corresponding to low, regular or medium and high solutions, designed to cause the reader to provide measurement in the low, medium and high ranges. The interface may guide the user through, for example, using these solutions to verify accurate operation of the strip reader.

The system may further include, in various embodiments, various linearity control test user interfaces. In an embodiment, linearity tests are run periodically and automated. In an embodiment, five tests are run for each linearity control cycle.

Advantageously, in various embodiments, automated quality control and linearity tests help ensure that the minimally invasive glucometer system 100 is calibrated and produces an accurate and precise result when measuring glucose levels in a user's blood across test strip lots and for various environmental conditions. In an embodiment, the information displayed may include time and date of last calibrations and next calibrations, may include information on how many calibrations have been accomplished and/or how many remain. For example, a timeline may advantageously indicate where in a calibration process the current measurements fall. Moreover, the timeline may include days, months, and years tabs to quickly organize information regarding device usage.

FIGS. 4L-4R illustrate exemplary glucose testing interfaces. For example, in FIGS. 4L-4M, the user is instructed to insert a test strip (such as the disposable glucose strip 110), and apply blood to the strip. In FIG. 4N the user is instructed to remove a test strip to proceed with a new test. In FIG. 4O the user is notified that the system is ready for a test to be run, for example, after a test strip has been inserted into the system. For example, the user may press the "Test" button of the user interface of FIG. 4O to begin a test on an inserted test strip. In FIG. 4P, a test is run and example test results are shown. In FIG. 4Q, various test results are shown in a table. For example, the user may store and/or view various test results taken at different times in a table, as shown. In an embodiment, the user may email test results to, for example, their physician. In FIG. 4R, an example user interface is shown in which the system indicates to the user that the test is incomplete as a test strip has been determined to be defective.

FIGS. 4S-4T illustrate exemplary informational user interfaces, such as instructions concerning the use of the minimally invasive glucometer system 100 and/or information about glucose measurements. Additionally, as shown in FIGS. 4S-4T, the system may display glucose measurements in various units (for example, mg/dL and/or mmol/L).

Advantageously, according to various embodiments the minimally invasive glucometer system enables minimally invasive blood glucose monitoring using a patient monitor. In other words, the same device that is used by the user for blood oxygen saturation monitoring (among other things) may also be used for blood glucose monitoring. The minimally invasive glucometer system may thus reduce the number of devices that a user must have to measure blood glucose levels and the various other levels that may be measured by an patient monitor (such as blood oxygen saturation ("SpO2"), pulse rate ("PR"), pethysmographic information, total hemoglobin (SpHb™), oxygen content (SpCO™), methemoglobin (SpMet®), carboxyhemoglobin (SpCO®) and PVI®).

Although the foregoing minimally invasive glucometer system has been described in terms of certain preferred embodiments, other embodiments will be apparent to those of ordinary skill in the art from the disclosure herein. For example, alternate protocols may be implemented or the like. Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to the appended claims.

All publications, patents, and patent applications mentioned in this specification are herein incorporated by reference to the same extent as if each individual publication, patent, or patent application was specifically and individually indicated to be incorporated by reference.

The various illustrative logical blocks, modules, routines, and algorithm steps described in connection with the embodiments disclosed herein may be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

The steps of a method, process, routine, or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of a non-transitory computer-readable storage medium. An example storage medium may be coupled to the processor such that the processor may read information from, and write information to, the storage medium. In the alternative, the storage medium may be integral to the processor. The processor and the storage medium may reside in an ASIC.

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y, and at least one of Z to each be present.

Moreover, terms used herein are intended to have their broad ordinary meaning understood within the art. The term "and/or" is intended to mean that one, any combination of two or more, or all combinations of the corresponding listed elements are appropriate; however, it is not intended to mean that all combinations must be accomplished.

What is claimed is:

1. A spot check monitoring system using a monitor configured to accept signals responsive to light attenuated by body tissue comprising:
   a housing that houses:
      a minimally invasive glucose reader configured to read a glucose level; and
      an encryption controller programmed to:
         provide authorization credentials to a patient monitor; and
         encrypt information, including said glucose level, transmitted from said minimally invasive glucose reader to said patient monitor; and
   said patient monitor in communication with said minimally invasive glucose reader;
   the patient monitor comprising a processor programmed to:
      operate as an oximeter;
      operate as a glucometer when in communication with said minimally invasive glucose reader;
      receive said authorization credentials;
      determine, based on said authorization credentials, that said minimally invasive glucose reader is authorized to communicate with said patient monitor;
      receive and unencrypt said information transmitted to said patient monitor; and
      display said glucose level.

2. The spot check monitoring system of claim 1, wherein said housing comprises a dongle.

3. The spot check monitoring system of claim 1, wherein said housing further houses a reader board, wherein said minimally invasive glucose reader is mounted on said reader board.

4. The spot check monitoring system of claim 3, wherein said housing further houses an encryption board, wherein said encryption controller is mounted on said encryption board.

5. The spot check monitoring system of claim 4, wherein said encryption board and said reader board are different boards.

6. The spot check monitoring system of claim 1, further comprising strips configured to be read by said minimally invasive glucose reader, wherein said strips comprise source identifying strips.

7. The spot check monitoring system of claim 1, wherein when said patient monitor is configured to operate as said oximeter, said patient monitor communicates with an optical sensor that outputs signals responsive to light attenuated by patient tissue carrying pulsing blood, said patient monitor receiving said signals and configured to process said signals to determine physiological parameters including at least an indication of oxygen saturation of the patient tissue.

8. The spot check monitoring system of claim 1, wherein said patient monitor comprises:
   a decryption chip configured to determine, based on said authorization credentials, that said minimally invasive glucose reader is authorized to communicate with said patient monitor.

9. An encrypted source-identifying glucose strip reader configured to change an oximeter into a glucometer, said reader comprising:
   a strip reader configured to accept samples on a strip and output a signal responsive to characteristics of said sample, said characteristics including a measure of glucose in said sample;
   a processor programmed to communicating with said strip reader to determine said measure of glucose from said sample and output data indicative of at least said measure;
   an encryption controller programmed to:
      provide authorization credentials to an oximeter configured to determine, based on the authorization credentials, that said reader is authorized to communicate with said oximeter, wherein said authorization credentials identify a source of said reader;
      receive said output data from said controller;
      encrypt said output data; and
      communicate, after encryption, said output data to said oximeter, wherein said oximeter is configured to modify its operation to present display indicia to a user of the oximeter, the display indicia responsive to said measure of said glucose in said sample; and
   a housing that houses said strip reader, said processor, and said encryption controller.

10. The reader of claim 9, further comprising a reader board, wherein said strip reader and said controller are mounted on said reader board.

11. The reader of claim 9, further comprising an encryption board, wherein said encryption controller is mounted on said encryption board.

12. The reader of claim 11, wherein said strip reader and said controller are mounted on said encryption board.

13. The reader of claim 9, wherein said housing comprises a dongle.

14. The reader of claim 13, wherein said dongle comprises a connector, said connector having a mechanical and pin layout that mechanically mates with an oximeter connector normally connected to a noninvasive optical sensor.

15. The reader of claim 13, wherein said strip reader and said controller comprise an OEM strip reader and controller.

16. The spot check monitoring system of claim 1, wherein said patient monitor in communication with said minimally invasive glucose reader is configured to be simultaneously used as a glucometer and an oximeter.

17. The spot check monitoring system of claim 8, wherein said encryption controller is configured to encrypt the information transmitted from said minimally invasive glucose reader using a public key and a private key cryptographic system.

* * * * *